United States Patent [19]

Grollier et al.

[11] Patent Number: 5,011,500
[45] Date of Patent: Apr. 30, 1991

[54] PROCESS FOR DYEING KERATINOUS FIBRES AND DYE COMPOSITION EMPLOYING INDOLE DERIVATIVES AND DIRECT NITRO DYES

[75] Inventors: Jean F. Grollier; Chantal Fourcadier, both of Paris, France

[73] Assignee: L'Oreal, Paris, France

[21] Appl. No.: 291,771

[22] Filed: Dec. 29, 1988

[30] Foreign Application Priority Data

Dec. 30, 1987 [LU] Luxembourg .............................. 87097

[51] Int. Cl.$^5$ ................................................ A61K 7/13
[52] U.S. Cl. ............................................ 8/410; 8/423; 8/406; 8/634
[58] Field of Search ................... 8/406, 407, 408, 410, 8/415, 423

[56] References Cited

U.S. PATENT DOCUMENTS

| | | | |
|---|---|---|---|
| 3,726,635 | 4/1973 | Kalopissis et al. | 8/415 |
| 4,690,685 | 9/1987 | Grollier et al. | 8/405 |
| 4,776,857 | 10/1988 | Corroll et al. | 8/405 |
| 4,804,385 | 2/1989 | Grollier et al. | 8/406 |
| 4,808,190 | 2/1989 | Grollier et al. | 8/406 |
| 4,822,375 | 4/1989 | Lang et al. | 8/408 |

FOREIGN PATENT DOCUMENTS

| | | | |
|---|---|---|---|
| 3031709 | 4/1982 | Fed. Rep. of Germany | 8/406 |
| 2082207 | 3/1982 | United Kingdom . | |
| 2164959 | 4/1986 | United Kingdom . | |
| 2185498 | 7/1987 | United Kingdom . | |

*Primary Examiner*—Paul Lieberman
*Assistant Examiner*—J. Darland
*Attorney, Agent, or Firm*—Cushman, Darby & Cushman

[57] ABSTRACT

Process for dyeing keratinous fibers, which comprises applying to these fibers at least one composition (A) containing, in a suitable medium for dyeing, at least one indole derivative and at least one substituted 2-nitro-para-phenylenediamine selected from the group consisting of 1-N-($\beta$-hydroxyethyl)amino-2-nitro-4-N', N'-(bis-$\beta$-hydroxyethyl)aminobenzene and 1-N-($\beta$-hydroxyethyl)amino-2-nitro-4-aminobenzene, the color being developed with the aid of an oxidizing system consisting of:

(i) iodide ions and hydrogen peroxide, the composition (A) additionally containing in this case either (a) iodide ions or (b) hydrogen peroxide and the application of this composition (A) being preceded or followed by the application of a composition (B) which contains, in a medium suitable for dyeing, either:
  (a) hydrogen peroxide at a pH of between 2 and 12 and preferably between 2 and 7 when the composition (A) contains iodide ions, or:
  (b) iodide ions at a pH of between 3 and 11 when the composition (A) contains hydrogen peroxide;
(ii) nitrites, the application of the composition (A) being followed, in this case, by the application of a composition (B) consisting of an aqueous composition exhibiting an acidic pH, the composition (A) or the composition (B) containing at least one nitrite; (iii) oxidizing agents selected from teh group consisting of periodic acid and periodates, sodium hypochlorite, potassium ferricyanide, silver oxide, Fenton's reagent, lead (IV) oxide caesium (V) sulphate, ammonium persulphate and ferric chloride, these oxidizing agents being present in the composition (A) or applied simultaneously or sequentially in a separate manner by means of a composition (B) containing them in a suitable medium for dyeing; or else
(iv) a permanganate or a dichromate, these oxidizing agents being applied by means of an aqueous composition (B) at a pH of 2 to 10, before the application of the composition (A).

37 Claims, No Drawings

PROCESS FOR DYEING KERATINOUS FIBRES AND DYE COMPOSITION EMPLOYING INDOLE DERIVATIVES AND DIRECT NITRO DYES

The invention relates to a new process for dyeing keratinous fibers, and more particularly human keratinous fibers such as hair, with indole derivatives combined with substituted 2-nitro-para-phenylenediamines and to the compositions used in this process.

It is well known that natural biosynthesis of eumelanins from tyrosine takes place in a number of stages. One of these consists in the formation of 5,6-dihydroxyindole which oxidizes to form a pigment which is one of the main constituents of eumelanin.

Many processes for dyeing hair using 5,6-dihydroxyindole have already been proposed in the past and, in particular, there is a known process which consists in dyeing hair in two separate stages, by applying to the hair a composition containing 5,6-dihydroxyindole in combination with iodide ions in a suitable medium for dyeing, this application being preceded or followed by the application of hydrogen peroxide at a pH of between 2 and 7. A process of this kind is described particularly in French Patent Application No. 2,593,061.

This last process is particularly noteworthy in its rapidity and owing to the fact that it does not change the mechanical properties of hair and in most cases produces black colors or various shades of grey and, in certain cases, brown and blond shades.

However, the use of 5,6-dihydroxyindole does not make it possible to obtain a sufficiently wide palette of various shades and highlights, and especially of the various shades of brown and of blond capable of being rich in highlights and particularly in demand in hair coloring.

Direct nitro dyes from the series of 2-nitro-para-phenylenediamines and their substituted derivatives, which are employed in dye compositions for dyeing keratinous fibers, are also known.

The applicants have found, and this forms the subject matter of the present invention, that it was possible to obtain various shades, rich in highlights by combining, in the same single composition, at least one indole derivative and at least one substituted 2-nitro-para-phenylenediamine chosen from 1-N-(β-hydroxyethyl)-amino-2-nitro-4-N',N'-(bis-β-hydroxyethyl)aminobenzene and 1-N-(β-hydroxyethyl)amino-2-nitro-4-aminobenzene, the color being developed by an oxidizing system.

It has found more particularly that the combination of these particular substituted 2-nitro-para-phenylenediamines with indole derivatives such as 5,6-dihydroxyindole developed using a hydrogen peroxide iodide oxidizing system resulted in shades exhibiting characteristics, particularly highlights, as well as robustness, which were particularly surprising in relation to the colors obtained with 5,6-dihydroxyindole or its derivatives employed by itself, as well as those obtained with other direct dyes usually employed in the field of hair dyeing.

A subject of the invention consists, therefore, of a process for dyeing keratinous fibers using indole derivatives and substituted 2-nitro-para-phenylenediamines, the colors being developed by an oxidizing system.

Another subject of the invention consists of dye compositions intended to be employed for dyeing keratinous fibres, using the combination defined above.

A further subject of the invention is dye outfits or kits, containing a number of components, permitting the use of the process outlined above.

Other subjects of the invention will become apparent on reading the description and the examples which follow.

The process for dyeing keratinous fibers, preferably human fibers, in accordance with the invention is characterized essentially by applying to these fibers at least one composition (A) containing, in a suitable medium for dyeing, at least one indole derivative and at least one substituted 2-nitro-para-phenylenediamine chosen from 1-N-(β-hydroxyethyl)amino-2-nitro-4-N',N'-(bis-β-hydroxyethyl)aminobenzene and 1-N-(β-hydroxyethyl-)amino-2-nitro-4-aminobenzene, the color being developed with the aid of an oxidizing system consisting of:

(i) iodide ions and hydrogen peroxide, the composition (A) additionally containing in this case either (a) iodide ions or (b) hydrogen peroxide and the application of the composition (A) being preceded or followed by the application of a composition (B) which contains, in a medium suitable for dyeing, either:
   (a) hydrogen peroxide at a pH of between 2 and 12 and preferably between 2 and 7 when the composition (A) contains iodide ions, or:
   (b) iodide ions at a pH of between 3 and 11 when the composition (A) contains hydrogen peroxide;

(ii) nitrites, the application of the composition (A) being followed by the application of a composition (B) consisting of an aqueous composition exhibiting an acidic pH, the composition (A) or (B) containing at least one nitrite;

(iii) oxidizing agents chosen from periodic acid and periodates, sodium hypochlorite, potassium ferricyanide, silver oxide, Fenton's reagent, lead (IV) oxide and caesium(V) sulphate, ammonium persulphate and ferric chloride, these oxidizing agents being present in the composition (A) or applied simultaneously or sequentially in a separate manner preferably after the composition (A) by means of a composition (B) containing them in a suitable medium for dyeing; or else (iv) permanganates or dichromates, these oxidizing agents being applied by means of an aqueous composition (B) at a pH of 2 to 10, before the application of the composition (A).

The application of the compositions (A) and (B) is preferably separated by a rinse.

In the process in accordance with the invention the indole derivatives preferably correspond to the formula:

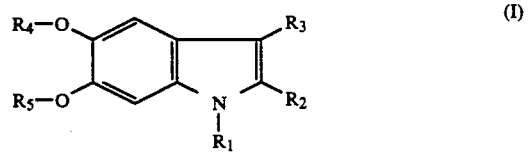

(I)

in which:
  $R_1$ denotes a hydrogen atom, a lower alkyl group or a $-SiR_6R_7R_8$ group;
  $R_2$ and $R_3$, which are identical or different, denote a hydrogen atom or else a lower alkyl group, a carboxyl group, a lower alkoxycarbonyl group or a $-COOSiR_6R_7R_8$ group;
  $R_4$ and $R_5$, which are identical or different, denote a hydrogen atom, a linear or branched $C_1$–$C_{20}$ alkyl group, a formyl group, a linear or branched $C_2$-$C_{20}$ acyl group, a linear or branched $C_3$-$C_{20}$ alkenoyl group, a —$SiR_6R_7R_8$ group, a —$P(O)(OR_9)_2$ group, an $R_9OSO_2$ group, or else $R_4$ and $R_5$, together with the oxygen atoms to which they are attached, form a ring optionally containing a carbonyl group, a methylene group, a thiocarbonyl group or a group:

$>P(O)OR_9$, or else $>CR_{10}R_{11}$;

$R_9$ and $R_{10}$ denoting a hydrogen atom or a lower alkyl group, $R_{11}$ denoting a lower alkoxy group or a mono-or dialkylamino group, $R_6$, $R_7$ and $R_8$, which are identical or different, denoting linear or branched lower alkyl groups, and the addition salts with inorganic or organic acids, as well as the corresponding alkali metal, alkaline-earth metal or amine salts.

The lower alkyl or alkoxy radicals preferably denote $C_1$-$C_5$ radicals.

Among the preferred compounds of the invention there will be mentioned 5,6-dihydroxyindole, 2-methyl-5,6-dihydroxyindole, 5-methoxy-6-hydroxyindole, (5 or 6)-acetoxy-(5 or 6)-hydroxy(6 or 5) indole or 2-carboxy-5,6-dihydroxyindole, 3-methyl-5,6-dihydroxyindole, and 2,3-dimethyl-5,6-dihydroxyindole and their salts.

In the first alternative form the iodide ion employed in accordance with the invention is preferably an alkali metal, alkaline-earth metal or ammonium iodide and more particularly potassium iodide.

The proportion of iodide ions in these compositions is preferably between 0.007 and 4% by weight, expressed as $I^-$ ions, and more particularly between 0.08 and 1.5% by weight expressed as $I^-$ ions relative to the total weight of the composition (A).

The hydrogen peroxide content is generally between 1 and 40 volumes and preferably between 2 and 20 volumes, and more particularly between 3 and 10 volumes.

The weight ratio of the indole derivative combined with the substituted 2-nitro-para-phenylenediamine(s) defined above, and the iodide ions, is preferably between 0.05 and 10 and more particularly between 0.5 and 2.

In the second alternative form of the process in accordance with the invention, the nitrites which can more particularly be employed are:

alkali metal, alkaline-earth metal or ammonium nitrites, or those of any other cation which is cosmetically acceptable when it is employed for dyeing living human hair;

organic nitrite derivatives such as, for example, amyl nitrite;

or else nitrite carriers, that is to say compounds which generate a nitrite on being converted.

The nitrites which are particularly preferred are sodium, potassium or ammonium nitrites.

The nitrite anion expressed in the form of $NO_2^-$ is present in sufficient quantities to develop a color with the indole derivative applied in the first stage. Its concentration is preferably between 0.02 and 1 mole/liter.

The pH of the composition (A) is preferably between 2 and 10.

The pH of the composition (B) is acidic and enables the color to be controlled. This pH is preferably between 2 and 6 and in particular is adjusted to approximately 3 for short contact times and for the darkest shades.

A preferred embodiment of the invention consists in applying the composition (A) containing the indole derivative in a first stage and the composition (B) containing a nitrite in an aqueous acidic medium in a second stage.

Another embodiment of the invention may consist in applying, in a first stage, a composition (A') containing, in a suitable medium for dyeing, the indole derivative in a neutral or alkaline medium and a nitrite. In this case, the hair is dyed by applying, in a second stage, a composition comprising a suitable aqueous medium for dyeing, adjusted to an acidic pH, preferably between 2 and 6.

According to the third alternative form, the oxidizing agent which is particularly preferred is sodium periodate. These oxidizing agents are preferably employed in proportions of 3 to 15% by weight relative to the total weight of the composition.

According to the fourth alternative form, potassium permanganate or sodium dichromate is preferably employed, these permanganates or dichromates being preferably employed at a molality greater than $10^{-3}$ mole/1000 g and preferably between $10^{-2}$ mole/1000 g and $10^{-1}$ mole/1000 g.

The pH of the composition containing the permanganate or dichromate anions is preferably between 2 and 5 and is adjusted to these values with inorganic acids.

The process for dyeing keratinous fibers, preferably human, in accordance with the invention is preferably implemented by applying to these fibers at least one composition (A) containing, in a suitable medium for dyeing, at least 5,6-dihydroxyindole, at least one substituted 2-nitro-para-phenylenediamine chosen from 1-N-($\beta$-hydroxyethyl)amino-2-nitro-4-N',N'-(bis-$\beta$-hydroxyethyl)aminobenzene and 1-N-($\beta$-hydroxyethyl)amino-2-nitro-4-aminobenzene in combination with iodide ions, the application by the application of a composition (B) which contains hydrogen peroxide at a pH of between 2 and 12 in a suitable aqueous medium for dyeing.

A particularly preferred use consists in applying, in the first stage, the composition (A) containing the iodide ions in the form of an alkali metal, alkaline-earth metal or ammonium iodide, 5,6-dihydroxyindole and the 2-nitro-para-phenylenediamine(s) defined above, and then, in a second stage, after an intermediate rinsing if desired, the composition (B) containing hydrogen peroxide.

The process in accordance with the invention is preferably applied to the dyeing of hair and in particular to that of living human hair, in which case the medium employed must be cosmetically acceptable.

According to a preferred embodiment, the keratinous fibers are rinsed between the two stages, which, inter alia, makes it possible to avoid staining the scalp when the composition is employed for dyeing human hair.

The invention may also be applied without intermediate rinsing, and this, in particular, allows the application time to be reduced.

The composition (A) employed in the process according to the invention, and forming another subject of the invention, is characterized essentially in that it contains, in a suitable medium for dyeing, an indole derivative of formula (I), at least one substituted 2-nitro-para-phenylenediamine chosen from 1-N-($\beta$-hydroxyethyl)amino-2-nitro-4-N',N'-(bis-$\beta$-hydroxyethyl)aminobenzene and 1-N-($\beta$-hydroxyethyl)amino-2-nitro-4-aminobenzene and at least iodide ions or nitrites.

In the compositions employed in accordance with the invention the indole derivative is generally present in proportions of between 0.01 and 5% by weight, and preferably between 0.03 and 3% by weight relative to the total weight of the composition (A). The proportion of substituted 2-nitro-para-phenylenediamine(s), such as defined above, is preferably between 0.01 and 5% by weight, and in particular between 0.1 and 3% by weight relative to the total weight of the composition (A).

The dyeing process in accordance with the invention is used by providing for application times for the various compositions applied in each of the various steps of the process of between 10 seconds and 45 minutes, and preferably of the order of 2 to 25 minutes and more particularly of the order of 2 to 10 minutes.

The applicants have found, in particular, that the process according to the invention made it possible to obtain quick colourings, penetrating well into the fibers and especially human keratinous fibers such as hair, without damaging them. These colorings have various shades and highlights and additionally exhibit an improved resistance to external agents and to permanent wave treatments and, in particular, have a superior resistance to light and/or to washing when compared with colorings obtained either with the indole derivative such as 5,6-dihydroxyindole by itself, or with substituted 2-nitro-para-phenylenediamines by themselves, with the oxidizing systems defined above.

The applicants have observed that hair dyed a number of times following its fresh growth, by virtue of the processes and of the compositions employed according to the invention was softer and more shiny and had better mechanical properties than hair dyed by using the processes and the compositions of the prior art.

The compositions used in the process in accordance with the invention may be presented in various forms such as liquids which are more or less thickened or gelled, creams, emulsions or foams, and may be packaged in aerosol devices, or else other suitable forms for performing the dyeing.

The suitable medium for dyeing is preferably an aqueous medium consisting of water or of a water-solvent(s) mixture. The solvents are chosen from organic solvents and preferably from ethyl alcohol, propyl or isopropyl alcohol, tert-butyl alcohol, ethylene glycol, ethylene glycol monomethyl, monoethyl and monobutyl ethers, ethylene glycol monoethyl ether acetate, propylene glycol, propylene glycol and dipropylene glycol monomethyl ethers and methyl lactate. The solvents which are particularly preferred are ethyl alcohol and propylene glycol.

According to another embodiment, the suitable medium for dyeing may consist of anhydrous solvents such as those defined preferably above, the composition being in this case either mixed with an aqueous medium at the time of use or applied to keratinous fibres wetted with an aqueous composition beforehand. In accordance with the invention, a medium containing less than 1% of water is called an anhydrous medium or solvent.

When the suitable medium for dyeing is aqueous, the pH of the composition (A) is preferably between 2 and 7 and in particular between 3.5 and 7.

When the suitable medium for dyeing consists of a water-solvent(s) mixture, the solvents are preferably employed in concentrations of between 0.5 and 75% by weight relative to the total weight of the composition and in particular between 2 and 50% and still more particularly between 2 and 20% by weight.

The compositions in accordance with the invention may contain all other adjuvants usually employed in dyeing keratinous fibers and in particular adjuvants which are cosmetically acceptable insofar as these compositions are applied for dyeing living human hair.

In this latter case, the compositions may, in particular, contain fatty amides in preferred proportions of 0.05 to 10% by weight, anionic, cationic, nonionic or amphoteric surface-active agents or mixtures thereof, which are preferably present in proportions of between 0.1 and 50% by weight, thickening agents, perfumes, sequestering agents, film-forming agents, treatment agents, dispersing agents, conditioning agents, preserving agents, opacifying agents, and agents for swelling the keratinous fibres.

The thickeners are chosen more particularly from sodium alginate, gum arabic, guar gum, heterobiopolysaccharides such as xanthan gum or scleroglucans, cellulose derivatives such as methyl cellulose, hydroxyethyl cellulose, hydroxypropyl methyl cellulose, the sodium salt of carboxymethyl cellulose and acrylic acid polymers, preferably crosslinked. It is also possible to employ inorganic thickening agents such as bentonite. These thickeners are employed by themselves or mixed and are preferably present in proportions of between 0.1 and 5% by weight relative to the total weight of the composition, and advantageously between 0.5 and 3% by weight.

The alkalizing agents which may be employed in these compositions may, in particular, be amines such as alkanolamines, alkylamines, and alkali metal or ammonium hydroxides or carbonates. The acidifying agents which may be employed in the compositions in accordance with the invention may be chosen from lactic acid, acetic acid, tartaric acid, phosphoric acid, hydrochloric acid and citric acid. Any other acceptable alkalizing or acidifying agent may, of course, be employed, especially in the case of cosmetic hair dyeing.

When the composition is employed in foam form, it may be packaged under pressure in an aerosol device in the presence of a propellent agent and of at least one foam generator. The foam generating agents may be anionic, cationic, nonionic or amphoteric foaming polymers or mixtures thereof, or surface-active agents of the type of those defined above.

With a view to the use of the process in accordance with the invention, the various compositions (A) and (B) may be packaged in a multicompartment device also known as a dyeing kit or outfit, containing all the components intended to be applied in the case of a single dyeing operation on keratinous fibres in successive applications with or without premixing.

Such devices are known per se and may comprise a first compartment containing the composition (A) comprising the indole derivative and the substituted 2-nitro-para-phenylenediamine(s) defined above in a suitable medium for dyeing and, in a second compartment, a composition (B) defined above.

When the medium containing the indole derivative and the substituted 2-nitro-para-phenylenediamine(s) is an anhydrous medium, a third compartment may be provided, containing a suitable aqueous medium for dyeing, intended to be mixed with the composition of the first compartment before use.

When the suitable medium for dyeing is aqueous, the composition of the first compartment preferably exhibits a pH of between 2 and 7, and in particular between 3.5 and 7. The pH of the composition (B) containing hydrogen peroxide is between 2 and 12, and preferably is acidic and between 2 and 7 and more particularly between 2 and 5.

The multicompartment devices which may be employed in accordance with the invention may be provided with means for mixing at the time of use, which are known per se, and their contents may be packaged in an inert atmosphere.

The process and the compositions employed in accordance with the invention may be used to dye natural or already dyed hair which has been permanent-waved or not, or straightened, or hair which has been strongly or slightly bleached and optionally permanent-waved. It is also possible to employ them for dyeing furs or wool.

The examples which follow are intended to illustrate the invention without, however, being limiting in character.

EXAMPLE 1

90% white natural hair is colored by applying a composition (A) as follows in succession and rinsing between the two applications:

| Composition (A): | | |
|---|---|---|
| 5,6-Dihydroxyindole | | 0.5 g |
| 1-N-(β-Hydroxyethyl)amino-2-nitro-4-N',N',(bis-β-hydroxyethyl)aminobenzene | | 0.25 g |
| Potassium iodide | | 1.0 g |
| Ethyl alcohol | | 10.0 g |
| Guar gum sold under the name "Jaguar HP60" by Celanese | | 1.0 g |
| Glycoside alkyl ether sold in a concentration of 60% AS under the name "Triton CG 110" by Seppic | | 5.0 g AS |
| Preserving agent q.s. | | |
| Natural pH = 5.95 | | |
| Water | q.s. | 100.0 g |

This is left in place for 10 minutes. After rinsing with water a composition (B) of 12.5-volume hydrogen peroxide is applied and is allowed to act for 5 minutes. After rinsing with water and shampooing, the hair is dark ash blond in color.

| Composition (B): | | |
|---|---|---|
| Hydrogen peroxide | | 3.75 g |
| Ammonium lauryl sulphate | | 6.7 g |
| Gum arabic | | 1.0 g |
| Perfume | q.s. | |
| 2-Amino-2-methyl-1-propanol | q.s. | pH 4 |
| Water | q.s. | 100.0 g |

EXAMPLE 2

90% white natural hair is colored by applying a composition (A) as follows in succession and rinsing between the two applications:

| | | |
|---|---|---|
| 5,6-Dihydroxyindole | | 0.5 g |
| 1-N-(β-Hydroxyethyl)amino-2-nitro-4-aminobenzene | | 0.25 g |
| Potassium iodide | | 1.0 g |
| Ethyl alcohol | | 10.0 g |
| Guar gum sold under the name "Jaguar HP 60" by Celanese | | 1.0 g |
| Glycoside alkyl ether sold in a concentration of 60% AS under the name "Triton CG 110" by Seppic | | 5.0 g AS |
| Preserving agent | q.s. | |
| Natural pH = 6 | | |
| Water | q.s. | 100.0 g |

This is left in place for 10 minutes. After rinsing with water, a composition (B) of 12.5-volume hydrogen peroxide, as described in Example 1, is applied and is allowed to act for 5 minutes. After rinsing with water and shampooing, the hair is dark golden mahogany blond in color.

EXAMPLE 3

| | | |
|---|---|---|
| 5,6-Dihydroxyindole | | 0.45 g |
| 1-N-(β-Hydroxyethyl)amino-2-nitro-4-aminobenzene | | 0.15 g |
| Potassium iodide | | 0.3 g |
| Ethylene glycol monobutyl ether | | 10.0 g |
| Sodium lauryl ether sulphate containing 2 moles of ethylene oxide, sold as a 30% solution in water under the name of Sactipon 8533 by Lever | | 3.5 g AS |
| Triethanolamine | q.s. | pH 7 |
| Preserving agents | q.s. | |
| Demineralized water | q.s. | 100.0 g |

This solution is applied for 20 minutes to 90% white natural grey hair. After rinsing, a hydrogen peroxide solution titrating at 20 volumes and adjusted to pH 8.5 with 2-methyl-2-amino-1-propanol is applied to this hair for 10 minutes. After a rinse and a suitable drying, the hair is colored a light ash gold brown shade.

EXAMPLE 4

| Composition (A): | | |
|---|---|---|
| Sodium iodide | | 0.4 g |
| Ethyl alcohol | | 5.0 g |
| Propylene glycol | | 5.0 g |
| Xanthan gum sold under the name of Rhodopol SC by Rhone-Poulenc | | 2.0 g |
| Preserving agent | q.s. | |
| Triethanolamine | q.s. | pH 6.5 |
| Demineralized water | q.s. | 100.0 g |

| Composition (B): | | |
|---|---|---|
| 5,6-Dihydroxyindole | | 0.6 g |
| 1-N-(β-Hydroxyethyl)amino-2-nitro-4-aminobenzene | | 0.35 g |
| 1-N-(β-Hydroxyethyl)amino-2-nitro-4-N',N',-(bis-β-hydroxyethyl)aminobenzene | | 0.15 g |
| Glycoside alkyl ether sold in a concentration of 60% AS under the name of Triton CG 110 by Seppic | | 7.5 g AS |
| Xanthan gum sold under the name of Rhodopol SC by Rhone-Poulenc | | 3.0 g |
| Ethyl alcohol | | 12.0 g |
| Preserving agent | q.s. | |
| Triethanolamine | q.s. | pH 6.5 |
| Demineralized water | q.s. | 100.0 g |

The composition (A) is applied for 15 minutes to 90% white natural grey hair, which is then rinsed. A mixture of equal weights of the composition (B) with a hydrogen peroxide at pH 3, titrating at 20 volumes, is then applied for 15 minutes, this mixture being made up at the time of use. The hair is then suitably rinsed and dried. A pearlescent red blond color is finally obtained on hair.

EXAMPLE 5

| | |
|---|---|
| 2-Methyl-5,6-dihydroxyindole hydrobromide | 0.6 g |
| 1-N-(β-Hydroxyethyl)amino-2-nitro-4-N',N',(bis-β-hydroxyethyl)aminobenzene | 0.3 g |
| Ethyl alcohol | 10.0 g |
| Potassium iodide | 0.5 g |
| Guar gum sold under the name of Jaguar HP 60 by Celanese | 1.0 g |
| Glycoside alkyl ether sold in a concentration of 60% AS under the name of Triton CG 110 by Seppic | 5.0 g AS |
| Preserving agents | q.s. |
| Triethanolamine | q.s. pH 6 |
| Demineralized water | q.s. 100.0 g |

This composition is applied for 20 minutes to 90% white natural grey hair. After a rinse, a hydrogen peroxide at pH 3 titrating at 12.5 volumes is applied for 10 minutes. After rinsing and sufficient drying, the hair is dyed a light golden ash blond shade.

EXAMPLE 6

Identical with Example 5, but the hydrogen peroxide solution employed is adjusted to pH 8 with triethanolamine before use.

A shade which is identical with that of Example 5, that is to say a light golden ash blond color is finally obtained.

EXAMPLE 7

| Composition (A): | |
|---|---|
| 5-Acetyloxy-6-hydroxyindole | 0.4 g |
| 1-N-(β-Hydroxyethyl)amino-2-nitro-4-aminobenzene | 0.10 g |
| Sodium iodide | 0.25 g |
| Ethylene glycol monobutyl ether | 15.0 g |
| Hydroxyethyl cellulose sold under the name of Natrosol 250 HHR by Aqualon | 1.5 g |
| Preserving agents | q.s. |
| Tartaric acid | q.s. pH 5.3 |
| Demineralized water | q.s. 100.0 g |

| Composition (B) containing 12.5 volumes H$_2$O$_2$: | |
|---|---|
| Hydrogen peroxide | 3.75 g |
| Ammonium lauryl sulphate | 6.7 g |
| Thickener | 1.0 g |
| Stabilizer | 0.03 g |
| Perfume | q.s. |
| 2-Amino-2-methyl-1-propanol | q.s. pH 3 |
| Water | q.s. 100.0 g |

Natural grey hair containing 90% white is treated with the above composition (A) for 15 minutes. After rinsing, the composition (B) is applied for 10 minutes. A further rinse and suitable drying are carried out. The hair is then color a very light pearlescent ash blond shade.

EXAMPLE 8

| Composition (A): | |
|---|---|
| 5,6-Dihydroxyindole | 0.5 g |
| 1-N-(β-Hydroxyethyl)amino-2-nitro-4-N',N',-(bis-β-hydroxyethyl)aminobenzene | 0.25 g |
| Ethylene glycol monoethyl ether | 8.0 g |
| Nonylphenol containing 9 moles of | 3.0 g |

| Composition (A): | | |
|---|---|---|
| ethylene oxide, sold by Henkel under the name Sinnopal NP 9 | | |
| Preserving agent | q.s. | |
| Hydrochloric acid | q.s. | pH 4.5 |
| Demineralized water | q.s. | 100.0 g |

| Composition (B): | | |
|---|---|---|
| Sodium periodate | | 4.0 g |
| Ethyl alcohol | | 5.0 g |
| Nonylphenol containing 9 moles of ethylene oxide sold by Henkel under the name Sinnopal NP 9 | | 1.5 g |
| Preserving agent | q.s. | |
| Triethanolamine | q.s. | pH 4 |
| Demineralized water | q.s. | 100.0 g |

90% white natural grey hair is treated with the composition (A) for 25 minutes. It is rinsed, and the composition (B) is applied for 15 minutes. A rinse and sufficient drying are applied. Hair color a brown shade is finally obtained.

EXAMPLE 9

The composition (A) of this Example is identical with the composition (A) of Example 8.

| Composition (B): | | |
|---|---|---|
| Sodium nitrite | | 2.0 g |
| Hydrochloric acid | q.s. | pH 3.8 |
| Demineralized water | q.s. | 100.0 g |

The composition (A) is applied to 90% white natural grey hair for 20 minutes. After rinsing, the composition (B) is applied for 5 minutes and is rinsed off. After appropriate drying, the hair is color an ash blond shade.

EXAMPLE 10

| | | |
|---|---|---|
| 5,6-Dihydroxyindole | | 0.3 g |
| 1-N-(β-Hydroxyethyl)amino-2-nitro-4-aminobenzene | | 0.1 g |
| Propylene glycol monomethyl ether | | 10.0 g |
| Potassium iodide | | 0.25 g |
| Ammonium lauryl sulphate sold under the name Empicol AL 30 by Marchon | | 3.0 g AS |
| Hydroxypropyl cellulose sold under the name of Klucel G by Hercules | | 0.8 g |
| Preserving agent | q.s. | |
| Citric acid | q.s. | pH 7 |
| Demineralized water | q.s. | 100.0 g |

90% white natural grey hair is pretreated for 15 minutes with hydrogen peroxide at pH 3, titrating at 30 volumes. After rinsing, the above composition is applied for 30 minutes. Another rinse and sufficient drying are applied. A dark pearlescent ash blond color is finally obtained.

EXAMPLE 11

| Composition (A): | | |
|---|---|---|
| Potassium permanganate | | 0.4 g |
| Hydrochloric acid | q.s. | pH 3 |
| Water | q.s. | 100.0 g |

| | |
|---|---|
| 5,6-Dihydroxyindole | 0.65 g |
| 1-N-(β-Hydroxyethyl)amino-2-nitro-4-N',N'-(bis-β-hydroxyethyl)aminobenzene | 0.20 g |
| Ethanol | 15.0 g |
| Nonylphenol containing 9 moles of ethylene oxide, sold under the name of Sinnopal NP9 by Henkel | 2.5 g |
| Preserving agent | q.s. |
| Natural pH = 5 | |
| Demineralized water | q.s. 100.0 g |

The composition (A) is applied to 90% white natural grey hair for 15 minutes. After rinsing, the composition (B) is applied for 10 minutes. A rinse and sufficient drying are applied. The hair is then color an ash brown shade.

We claim:

1. A process for dyeing keratinous fibers comprising applying to said fibers at least one composition (A) containing in a medium suitable for dyeing said fibers, (1) at least one indole derivative having the formula

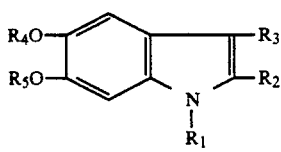

(I)

wherein
R₁ represents hydrogen, lower alkyl or —SiR₆R₇R₈,
R₂ and R₃, each independently, represent hydrogen, lower alkyl, carboxyl, lower alkoxycarbonyl or —COOSiR₆R₇R₈,
R₄ and R₅, each independently, represent hydrogen, linear or branched C₁-C₂₀ alkyl, formyl, linear or branched C₂-C₂₀ acyl, linear or branched C₃-C₂₀ alkenoyl, SiR₆R₇R₈, —P(O) (OR₉)₂ or R₉OSO₂, or R₄ and R₅ together with the oxygen atoms to which they are attached form a ring optionally containing a carbonyl group, a methylene group, a thiocarbonyl group, a >P(O)OR₉ group or a >CR₁₀R₁₁ group,
R₉ and R₁₀ represent hydrogen or lower alkyl, R₁₁ represents lower alkoxy, monoalkylamino or dialkylamino, and
R₆, R₇ and R₈, each independently, represent linear or branched alkyl, and
the acid addition salt thereof with an inorganic or organic acid or the corresponding alkali metal, alkaline earth metal or amine salt thereof, said indole derivative being present in said composition (A) in an amount ranging from 0.01 to 5 percent by weight based on the total weight of said composition (A) and
(2) at least one substituted 2-nitro-paraphenylene diamine selected from the group consisting of 1-N-(β-hydroxyethyl)amino-2-nitro-4-N', N'-(bis-β-hydroxyethyl) aminobenzene and 1-N-(β-hydroxyethyl)amino-2-nitro-4-aminobenzene, present in an amount ranging from 0.01 to 5 percent by weight based on the total weight of said composition (A), and
developing a color on said fibers using an oxidizing system selected from the group consisting of:
(i) a source of iodide ions and hydrogen peroxide, in which case said composition (A) contains either (a) a source iodide ions or (b) hydrogen peroxide and the application of said composition (A) is preceded or followed by the application of composition (B) comprising in a medium suitable for dyeing said fibers
(a') hydrogen peroxide at a pH ranging from 2 to 12 when said composition (A) contains a source iodide ions, or
(b') a source of iodide ions at a pH ranging from 3 to 11 when said composition (A) contains hydrogen peroxide;
(ii) a nitrite source, in which case the application of said composition (A) is followed by the application of composition (B') comprising an aqueous composition having an acidic pH, said composition (A) or said composition (B') containing at least one said nitrite source;
(iii) an oxidizing agent selected from the group consisting of periodic acid, a periodate, sodium hypochlorite, potassium ferricyanide, silver oxide, Fenton's reagent, lead (IV) oxide, cesium (V) sulphate, ammonium persulfate and ferric chloride, said oxidizing agent being present in said composition (A) or being applied to said fibers simultaneously or sequentially in a composition (B") comprising a medium suitable for dyeing said fibers and said oxidizing agent; and
(iv) an oxidizing agent selected from the group consisting of a permanganate and a dichromate, said oxidizing agent being present in an aqueous composition (B''') having a pH ranging from 2 to 10, said composition (B''') being applied to said fibers prior to the application of said composition (A) thereto.

2. The process of claim 1 wherein said source of iodide ions is selected from the group consisting of an alkali metal iodide, an alkaline earth metal iodide and ammonium iodide.

3. The process of claim 2 wherein the amount of said iodide ions ranges between 0.007 and 4 percent by weight, expressed as I⁻ ions, relative to the total weight of said composition.

4. The process of claim 2 wherein the amount of said iodide ions ranges between 0.08 and 1.5 percent by weight, expressed as I⁻ ions, relative to the total weight of said composition.

5. The process of claim 1 wherein the hydrogen peroxide content is between 1 and 40 volumes.

6. The process of claim 1 wherein the hydrogen peroxide content is between 2 and 20 volumes.

7. The process of claim 1 wherein the weight ratio of said indole derivative combined with said substituted 2-nitro-paraphenylene diamine to said iodide ions ranges from 0.05 to 10.

8. The process of claim 1 wherein the weight ratio of said indole derivative combined with said substituted 2-nitro-paraphenylene diamine to said iodide ions ranges from 0.5 to 2.

9. The process of claim 1 wherein said nitrite source is selected from the group consisting of an alkali metal nitrite, an alkaline earth metal nitrite, ammonium nitrite, or an organic nitrite.

10. The process of claim 1 wherein said nitrite, expressed in the form of $NO_2^-$, is present in an amount ranging from 0.02 to 1 mole/liter.

11. The process of claim 1 wherein said oxidizing system is sodium periodate.

12. The process of claim 1 wherein said permanganate is potassium permanganate present in an amount greater than $10^{-3}$ mole/1000 g.

13. The process of claim 1 wherein said dichromate is sodium dichromate present in an amount greater than $10^{-3}$ mole/1000 g.

14. The process of claim 1 wherein said indole derivative is selected from the group consisting of 5,6-dihydroxyindole, 2-methyl-5,6-dihydroxyindole, 5-methoxy-6-hydroxyindole, 6-acetoxy-5-hydroxyindole, 5-acetoxy-6-hydroxyindole, a mixture of 6-acetoxy-5-hydroxyindole and 5-acetoxy-6-hydroxyindole, 2-carboxy-5,6-dihydroxyindole, 3-methyl-5,6-dihydroxyindole and 2,3-dimethyl-5,6-dihydroxyindole and a salt thereof.

15. A process for dyeing keratinous fibers comprising applying to said fibers at least one composition (A) containing, in a medium suitable for dyeing said fibers, at least 5,6-dihydroxyindole present in an amount ranging from 0.01 to 5 percent by weight of composition A and at least one substituted 2-nitro-paraphenylene diamine selected from the group consisting of 1-N-(β-hydroxyethyl) amino-2-nitro-4-N',N'-(bis-β-hydroxyethyl) aminobenzene and 1-N-(β-hydroxyethyl) amino-2-nitro-4-aminobenzene said amino benzene present in an amount ranging from 0.01 to 5 percent by weight of composition A in combination with a source of iodide ions, the application of said composition (A) being preceded or followed by the application to said fibers of composition (B) containing hydrogen peroxide in a medium suitable for dyeing said fibers, said composition (B) having a pH ranging from 2 to 12.

16. The process of claim 15 which comprises applying to said fibers, in a first stage, said composition (A) containing aid 5,6-dihydroxyindole, said substituted 2-nitro-paraphenylenediamine and said source of iodide ions in the form of an alkali metal iodide, an alkaline earth metal iodide or ammonium iodide and, in a second stage, applying said composition (B) to said fibers.

17. The process of claim 1 wherein the stages of said process are separated by a rinsing stage.

18. The process of claim 1 wherein the stages of said process are carried out without an intermediate rinsing stage.

19. The process of claim 1 wherein said compositions (A), (B), (B'), (B") and (B''') are permitted to remain in contact with said fibers for a period of time ranging from 10 seconds to 45 minutes.

20. The process of claim 1 wherein said compositions (A), (B), (B'), (B") and (B''') are permitted to remain in contact with said fibers for a period of time ranging from 2 to 25 minutes.

21. The process of claim 1 wherein said indole derivative is present in said composition (A) in an amount ranging from 0.03 to 3 percent by weight based on the total weight of said composition (A).

22. The process of claim 1 wherein said substituted 2-nitro-paraphenylene diamine is present in said composition (A) in an amount ranging from 0.1 to 3 percent by weight based on the total weight of said composition (A).

23. The process of claim 1 wherein said medium suitable for dyeing said fibers is an aqueous medium comprising water or a mixture of water and an organic solvent, said aqueous medium having a pH ranging from 2 to 7.

24. The process of claim 23 wherein said aqueous medium has a pH ranging from 3.5 to 7.

25. The process of claim 1 wherein said medium suitable for dyeing said fibers is an anhydrous solvent.

26. The process of claim 23 wherein said organic solvent is selected from the group consisting of ethyl alcohol, propyl alcohol, isopropyl alcohol, tert. butyl alcohol, ethylene glycol, ethylene glycol monomethyl ether, ethylene glycol monoethyl ether, ethylene glycol monobutyl ether, ethylene glycol monoethyl ether acetate, propylene glycol, propylene glycol monomethyl ether, dipropylene glycol monomethyl ether and methyl lactate.

27. The process of claim 25 wherein said anhydrous solvent is selected from the group consisting of ethyl alcohol, propyl alcohol, isopropyl alcohol, tert. butyl alcohol, ethylene glycol monomethyl ether, ethylene glycol monoethyl ether, ethylene glycol monobutyl ether, ethylene glycol monoethyl ether acetate, propylene glycol, propylene glycol monomethyl ether, dipropylene glycol monomethyl ether and methyl lactate.

28. The process of claim 1 wherein one or more of said compositions also include at least one adjuvant selected from the group consisting of a fatty amide; an anionic, cationic, nonionic or amphoteric surface-active agent or a mixture thereof; a thickening agent; a perfume; a sequestering agent; a film-forming agent; a treatment agent; a dispersing agent; a conditioning agent; a preservative; an opacifying agent; and an agent for swelling keratinous fibers.

29. A composition for dyeing keratinous fibers comprising in a medium suitable for dyeing keratinous fibers (i) at least one indole derivative having the formula

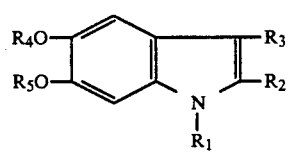

(I)

wherein $R_1$ represents hydrogen, lower alkyl or $-SiR_6R_7R_8$, $R_2$ and $R_3$, each independently, represent hydrogen, lower alkyl, carboxyl, lower alkoxycarbonyl or $-COOSiR_6R_7R_8$, $R_4$ and $R_5$, each independently, represent hydrogen, linear or branched $C_1-C_{20}$ alkyl, formyl, linear or branched $C_2-C_{20}$ acyl, linear or branched $C_3-C_{20}$ alkenoyl, $-SiR_6R_7R_8$, $-P(O)(OR_9)_2$ or $R_9OSO_2$, or $R_4$ and $R_5$ together with the oxygen atoms to which they are attached form a ring optionally containing a carbonyl group, a methylene group, a thiocarbonyl group, a $>P(O)OR_9$ group or a $>CR_{10}R_{11}$ group, $R_9$ and $R_{10}$ represent hydrogen or lower alkyl, $R_{11}$ represents lower alkoxy, monoalkylamino or dialkylamino, and $R_6$, $R_7$ and $R_8$, each independently, represent linear or branched alkyl, and the acid addition salt thereof with an inorganic or organic acid or the corresponding alkali metal, alkaline earth metal or amine salt therefor, said indole being present in an amount ranging from 0.01 to 5 percent by weight based on the total weight of said composition, (ii) at least one substituted 2-nitro-paraphenylene diamine selected from the group consisting of 1-N-(β-hydroxyethyl) amino-2-nitro-4-N',N'-(bis-β- hydroxyethyl) aminobenzene and 1-N-(β-hydroxyethyl) amino-2-nitro-4-aminobenzene present in an amount ranging from 0.01 to 5 percent by weight based on the total weight of said composition, and (iii) a source of iodide ions or a nitrite source.

30. A composition for dyeing keratinous fibers comprising in a medium suitable for dyeing keratinous fibers (i) at least 5,6-dihydroxyindole, (ii) at least one substituted 2-nitroparaphenylene diamine selected from the group consisting of 1-N-(β-hydroxyethyl) amino-2-nitro-4-N',N'-(bis-β-hydroxyethyl) aminobenzene and 1-N-(β-hydroxyethyl) amino-2-nitro-4-aminobenzene, and (iii) a source of iodide ions, said dihydroxyindole and said aminobenzene both being present in an amount ranging from 0.01 to 5 percent by total weight of said composition.

31. A multi compartment kit for use in keratinous fibers comprising
    (a) a first compartment containing composition (A) as defined in claim 35 and
    (b) a second compartment containing composition (B) as defined in claim 35.

32. The multicompartment kit of claim 31 wherein said composition (A) housed in said first compartment contains a source of iodide ions and said composition (B) housed in said second compartment is an aqueous hydrogen peroxide composition having a pH ranging from 2 to 12.

33. The multicompartment kit of claim 31 wherein the medium suitable for dyeing keratinous fibers of said composition (A) housed in said first compartment is an aqueous medium having a pH ranging from 2 to 7 and said composition (B) housed in said second compartment is an aqueous hydrogen peroxide composition having a pH ranging from 2 to 7.

34. The multicompartment kit of claim 31 which contains a third compartment housing an aqueous medium for admixture at the time of use with the contents of said first compartment housing composition (A) in an anhydrous organic solvent.

35. A multicompartment kit for use in dyeing keratinous fibers comprising
    (a) a first compartment housing composition (A) as defined in claim 1 and
    (b) a second compartment housing, in an aqueous medium suitable for dyeing keratinous fibers, a permanganate, a dichromate or a periodate.

36. A multicompartment kit for use in dyeing keratinous fibers comprising
    (a) a first compartment housing composition (A) as defined in claim 1 and
    (b) a second compartment housing, in an aqueous medium suitable for dyeing keratinous fibers and having an acidic pH, a nitrite source.

37. A multicompartment kit for use in dyeing keratinous fibers comprising
    (a) a first compartment housing (i) at least one indole derivative having the formula

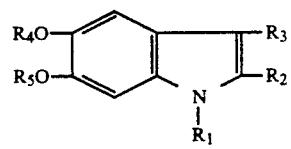

(I)

wherein
R₁ represents hydrogen, lower alkyl or —SiR₆R₇R₈,
R₂ and R₃, each independently, represent hydrogen, lower alkyl, carboxyl, lower alkoxycarbonyl or —COOSiR₆R₇R₈,
R₄ and R₅, each independently, represent hydrogen, linear or branched C₁–C₂₀ alkyl, formyl, linear or branched C₂–C₂₀ acyl, linear or branched C₃–C₂₀ alkenoyl, —SiR₆R₇R₈, —P(O) (OR₉)₂ or R₉OSO₂, or R₄ and R₅ together with the oxygen atoms to which they are attached form a ring optionally containing a carbonyl group, a methylene group, a thiocarbonyl group, a >P(O)OR₉ group or a >CR₁₀R₁₁ group,
R₉ and R₁₀ represent hydrogen or lower alkyl,
R₁₁ represents lower alkoxy, monoalkylamino or dialkylamino, and
R₆, R₇ and R₈, each independently, represent linear or branched alkyl, and
the acid addition salt thereof with an inorganic or organic acid or the corresponding alkali metal, alkaline earth metal or amine salt therefor,
(ii) a substituted 2-nitro-paraphenylene diamine selected from the group consisting of 1-N-(β-hydroxyethyl) amino-2-nitro-4-N',N'-(bis-β-hydroxyethyl) amino benzene and 1-N-(β-hydroxyethyl) amino-2-nitro-4-aminobenzene and (iii) a source of iodide ions or a nitrite source and
(b) a second compartment containing an acidic aqueous composition said indole derivative and said aminobenzene both being present in such amounts that when the composition of compartment (a) is mixed with the composition of compartment (b), said indole derivative and said aminobenze both individually amount to from 0.01 to 5 percent by weight of the total composition.

* * * * *